United States Patent [19]

Reusser et al.

[11] 4,431,855

[45] Feb. 14, 1984

[54] REDUCED POLYMER FORMATION IN DISPROPORTIONATION REACTION BY ADDITION OF CO TO FEED

[75] Inventors: Robert E. Reusser, Bartlesville, Okla.; Donald G. Kuper, Houston, Tex.

[73] Assignee: Phillips Petroleum Company, Bartlesville, Okla.

[21] Appl. No.: 413,203

[22] Filed: Aug. 30, 1982

[51] Int. Cl.³ .............................................. C07C 3/62
[52] U.S. Cl. ................................... 585/360; 585/364; 585/646; 585/645
[58] Field of Search ............... 585/360, 362, 364, 600, 585/643, 646, 645

[56] References Cited

U.S. PATENT DOCUMENTS

| 3,567,789 | 3/1971 | Harrison | 585/364 |
| 3,634,538 | 1/1972 | Steffgen | 585/646 |
| 3,637,892 | 1/1972 | McGrath et al. | 585/645 |
| 3,872,180 | 3/1975 | Nakatomi et al. | 585/646 |
| 3,981,940 | 9/1976 | Zuech | 260/683 D |

FOREIGN PATENT DOCUMENTS 422240 12/1971 U.S.S.R. ............... 585/646

Primary Examiner—Delbert E. Gantz
Assistant Examiner—A. Pal

[57] ABSTRACT

In an olefin disproportionation reaction, the formation of undesirable polymer is inhibited by the inclusion of a small amount of carbon monoxide in the feed.

15 Claims, No Drawings

REDUCED POLYMER FORMATION IN DISPROPORTIONATION REACTION BY ADDITION OF CO TO FEED

BACKGROUND OF THE INVENTION

This invention relates to the disproportionation of olefin hyrocarbons.

By disproportionation is meant the conversion of an olefin hydrocarbon to a product having a different number of carbon atoms. In one aspect, this involves the reaction of two similar molecules to give a mixture of products having respectively a greater and a lesser number of carbon atoms than the starting material. For instance, two molecules of 4-vinylcyclohexene react to give bis-cyclohexenylethylene and ethylene. In a second embodiment, a cyclic olefin and a second olefin serve as feed components to give cleavage of the cyclic olefin which may result in either different products or, assuming the conversion is complete a single product as for instance in the reaction of ethylene and 1,5,9-cyclododecatriene to give 1,5-hexadiene. In a third aspect, a mixture of olefins as for instance 1-hexene and 1-octene react to give 5-decene, 5-dodecene, and 7-tetradecene.

In these reactions, it is readily apparent that the presence of olefinic materials carries with it the constant potential for formation of undesirable polymeric products which both reduce the production levels of the desired products and cause plugging of the reaction equipment. These polymeric products may be formed from the starting reactants, intermediates formed during the reaction or the final product or any combination thereof.

SUMMARY OF THE INVENTION

It is an object of this invention to reduce or eliminate polymer formation in olefin disproportionation reactions;

It is a further object of this invention to avoid plugging of reaction apparatus in olefin disproportionation reactions;

It is yet a further object of this invention to reduce or eliminate plugging in olefin disproportionation reactions without adversely affecting selectivity or conversion; and It is yet a further object of this invention to provide a process for high selectivity, high conversion olefin disproportionation reactions.

In accordance with this invention, carbon monoxide is introduced along with the feed in an olefin disproportionation reaction.

DESCRIPTION OF THE PREFERRED EMBODIMENTS

Olefin disproportionation reactions are generally known, as disclosed in Banks, U.S. Pat. No. 3,261,879, the disclosure of which is hereby incorporated by reference. A more specific reaction to produce bis-cyclohexenyl olefins is disclosed in Crain, U.S. Pat. No. 3,463,828, the disclosure of which is hereby incorporated by reference.

The catalysts useful in this invention are conventional olefin disproportionation catalysts as disclosed in said Banks and Crain patents. The preferred catalyst in this invention is molybdenum oxide used alone or more preferably in combination with cobalt oxide, (generally referred to as "cobalt-molybdenum" catalyst) which catalyst is generally supported on a material such as alumina. Also suitable is tungsten oxide generally supported on a support such as silica. These molybdenum, cobalt-molybdenum, or tungsten catalysts are readily available as commercial products. Examples of suitable commercial catalysts other than those used in the examples are:

| Composition | Manufacturer (#) |
|---|---|
| 3% CoO; 12% MoO$_3$; 85% Al$_2$O$_3$ | Harshaw 0603; |
| 3% CoO; 11% MoO$_3$; 86% Al$_2$O$_3$ | Nalco 471; and |
| 10% MoO$_3$; 90% Al$_2$O$_3$ | Harshaw 1201T. |

The invention is suitable for reducing polymer formation in the disproportionation of any monomer which is susceptible to disproportionation. The examples of such monomers are set out in said Banks and Crain patents and also in Reusser, U.S. Pat. No. 3,836,480, the disclosure of which is hereby incorporated by reference. Briefly, compounds suitable for disproportionation according to the invention are acyclic 1- and 2-alkenes, alkyl, and aryl derivatives thereof having from 3 to 30, preferably 4-20 carbon atoms per molecule. Some specific examples of such olefins are propylene, 1-butene, 2-butene, 1-pentene, 2-pentene, 1-hexene, 2-heptene, 1-octene, 2-nonene, 1-dodecene, 2-tetradecene, 1-hexadecene, 2-methyl-1-butene, 2-methyl-2-butene, 3-methyl-1-butene, 1-phenylbutene-2, and 3-heptene. To generalize with respect to feed, C$_3$-C$_{30}$ acyclic, cyclic and bicyclic mono-, di-, or polyolefin hydrocarbons preferably those which are nonconjugated are suitable. This encompasses compounds such as 1,5,9-cyclododecatriene and cyclododecene reacted with ethylene and cross-reactants, 1-hexene and 1-octene. Particularly suitable are substituted compounds of the general formula

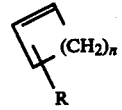

where n equals 1 to 27 and R is 1 or more of the following substituents: alkyl, cycloalkyl, aryl, and alkenyl. This encompasses the preferred reactant vinyl cyclohexene and more broadly the alkenyl substituted cycloalkenes shown in said Crain patent.

Thus, the invention is of particular utility in a method for synthesizing bis(cycloalkenyl)-substituted olefins which comprises passing an alkenyl-substituted cycloalkene having the formula

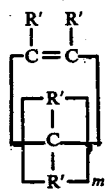

wherein one R' is

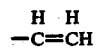

wherein the remaining R's are selected from the group consisting of hydrogen and alkyl radicals containing from 1 to 10 carbon atoms, wherein m is 4, and wherein the total carbon atoms in one of said alkenyl-substituted cycloalkenes does not exceed 20 to a reaction zone along with 0.1 to 50 weight percent CO based on the weight of said alkenyl-substituted cycloalkene; contacting said alkenyl-substituted cycloalkene with an effective catalytic amount of a catalyst resulting from the admixture of one of molybdenum oxide, cobalt oxide, tungsten oxide, molybdenum hexacarbonyl, tungsten hexacarbonyl, ammonium tungstate, and molybdenum, cobalt, and tungsten materials convertible to the oxide on calcination and one of alumina- and silica-containing support under conditions of temperature and pressure sufficient to form bis(cycloalkenyl)-substituted olefins of the formula

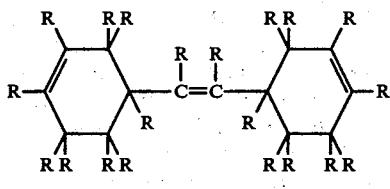

wherein R is at least one member selected from the group consisting of hydrogen and alkyl containing from 1 to 10 carbon atoms and recovering said bis(cycloalkenyl) substituted olefin. Here, the catalyst may consist essentially of alumina and between 0.1 and 30 weight percent of molybdenum oxide. Optionally, the catalyst may contain 0.1 to 10 weight percent cobalt oxide, 0.1 to 30 weight percent molybdenum oxide and the rest alumina.

As an illustrative embodiment, 1,2-bis(3-cyclohexen-1-yl) ethylene is formed by contacting 4-vinylcyclohexene with a catalyst consisting essentially of from 3 to 15 weight percent molybdenum oxide, from 1 to 5 weight percent cobalt oxide, and from 96 to 80 weight percent aluminum oxide which aluminum oxide has a surface area ranging from 25–300, preferably 50–250 square meters per gram at a temperature ranging from 75°–200° C. for a period of time sufficient to obtain a 25 percent conversion and recovering the 1,2-bis(3-cyclohexen-1-yl)ethylene product.

The reaction conditions are conventional in the art and more specifically can be as set out in said Banks patent.

The process can be carried out either batchwise or continuously, using a fixed catalyst bed, or a stirrer equipped reactor or other mobile catalyst contacting processes as well as any other well known contacting technique. Preferred reaction conditions, for instance temperature, pressure, and flow rates vary somewhat depending on the specific catalyst composition, the particular feed olefin, and the desired products. The process is carried out generally at a temperature of 77°–572° F. (25°–300° C.), preferably 250°–400° F. (121°–204° C.). Pressure can be any convenient pressure, for instance 0 to 1500 psig. Although the disproportionation reaction of this invention is essentially independent of pressure, for most economical operation considering combination with other steps of a complete plant operation including, for example, product separation and recovery, a pressure range of 50 to 500 psig can be used most conveniently.

The operable range of contact time for the process of this invention depends primarily upon the operating temperature and the activity of the catalyst which is influenced by surface area, promoter concentration, and activation temperature. In general, the distribution of products is not drastically altered by variation in contact time. However, long contact times in general favor the production of larger proportions of higher molecular weight products. In general, shorter contact times are associated with higher temperatures, but when larger amounts of higher molecular weight products are desired, a suitable combination of contact time and temperature is selected.

A weight hourly space velocity of 0.1 to 1,000, preferably 0.5 to 20, more preferably 1 to 10 parts by weight of hydrocarbon feed per part by weight of catalyst is suitable. Higher space velocities in general are associated with higher reaction temperatures. In general contact times in the range of 0.5 seconds to 10 hours are used.

The process may be carried out in the presence or absence of an inert diluent with the amount of diluent generally ranging from 0 to 90 volume percent of the reaction mixture. Suitable diluents include saturated hydrocarbons such as alkanes and cycloalkanes. Some examples are cyclohexane, cycloheptane, hexanes, octanes, decalin, and mixtures thereof.

Of course, the important consideration is the contact time between active catalyst and monomer. Hence, in the case of tungsten catalysts which are more likely to contain inert carrier material, higher space hourly weight velocities of feed are generally utilized.

Carbon monoxide is used in an amount within the range of 0.1 to 50, preferably 0.5 to 25 weight percent based on the weight of the olefin feed. In the event a diluent is used, the calculation is still based on the weight of the feed only, without regard to the diluent. The carbon monoxide is simply metered into the reaction vessel, preferably along with the feed. In a less preferred embodiment, it can be introduced as a separate stream into the vessel. As with the feed itself, an inert diluent can be used in order to facilitate the metering of the carbon monoxide. Gases such as nitrogen, argon and other inert gases could be used for such purpose, however generally, there will be no diluent with the carbon monoxide.

After the reaction period, the products are separated and isolated using conventional techniques.

EXAMPLE I

The reactor employed in Example I was a ¼"×20" stainless steel pipe, which had a pre-heat zone packed with glass beads and a post reaction zone packed with glass beads. Thus, the top 7½–8" of the pipe was packed with glass beads, followed by a ½–1" glass wool plug. Then, about 20 mL of catalyst (filling about 8" of pipe) were loaded followed by another glass wool plug, and the remainder of the bed (about 4–4½") filled with glass beads.

Catalysts employed in the following examples are identified as follows:

| Catalyst | Composition | Manufacturer (#) |
|---|---|---|
| A | 4% CoO; 15% MoO$_3$; 81% Al$_2$O$_3$ | American Cyanamid (HDS-2) |
| A' | A + 0.25 wt. % KOH | |
| A" | A + 0.75 wt. % KOH | |

Typically, catalyst was activated by heating in air for 2-3 hours at about 540° C. (1000° F.), then pre-reduced by introducing a carbon monoxide flow for about 15 minutes while maintaining catalyst at 540° C. Reactor was then cooled to desired reaction temperature, typically 130° C. (267° F.) under a CO atmosphere, then olefin feed introduced.

Samples were analyzed by gas liquid chromatography (glc) employing a ⅛"×20' 10% SE-30 on Chromosorb packed column. Conversion/selectivity values were calculated using glc area percent. Thus, conversion is determined by subtracting starting material area percent from 100. Selectivity is determined by dividing total area percent for primary disproportionation products by the conversion.

The disproportionation reactor was loaded with 21 gm of catalyst A' (0.25 wt. % KOH (based on K metal) treated American Cyanamid HDS-2 catalyst). An equimolar mixture of 1-hexene and 1-octene was introduced at a flow rate of about 30 mL/hr. After about 4 hours on stream, polymer formation was apparent as evidenced by reactor plugging giving pressure rise and precipitation of white solid in the effluent. The white precipitate was analyzed by infrared as a KBr disc and showed absorptions at 720, 1370, 1460, 2850, and 2920 $cm^{-1}$ which indicate a long-chain polyethylene-like hydrocarbon material.

Several more experiments were carried out with the same feed at a variety of WHSV, reaction times, pressures, and the like in the absence and presence of CO as co-feed. Results are summarized in Table I.

As is shown by Run 3, the problem of polymer formation exists whether or not the catalyst is given a CO pretreatment. A separate matter from use of CO in the feed is the presence or absence of CO treatment of the catalyst itself.

EXAMPLE II

The self-reaction of vinyl-cyclohexene over a disproportionation catalyst to give bis(cyclohexenyl)ethylene was carried out with a CO-activated cobalt molybdate catalyst. The general procedure described above was employed, except 40 g of catalyst was employed with no glass beads. The reaction conditions employed and experimental results are presented in Table II.

TABLE II

| Run No. | Feed Rates* VCH, mL/hr | CO, mL/min | | Reaction Conditions Temp., °C. | Press., psig | Time, hr | WHSV | Conversion | Selectivity | Polymer |
|---|---|---|---|---|---|---|---|---|---|---|
| 1 | 50 | — | | 130 | 50 | 2 | 1 | 20.2 | 89.5 | Yes |
| 2 | 140 | 110 | (7.1) | 130 | 50 | 2 | 3 | <2 | 77 | None |
| 2a | 50 | 110 | (20) | 130 | 50 | 2 | 1 | 3.5 | 83 | None |
| 3 | 45 | 40 | (8) | 130 | 50 | 5 | 1 | 8.2 | 81.5 | None |
| 4 | 50 | 40 | (7.2) | 130 | 50 | 4 | 1 | 14.7 | 87.8 | None |
| 5 | 50 | 35 | (6) | 130 | 50 | 4 | 1 | 10.2 | 88.1 | None |
| 6 | 50 | 35 | (6) | 150 | 50 | 4.5 | 1 | 16.5 | 87.5 | None |
| 7 | 50 | 35 | (6) | 150 | 50 | 2 | 1 | 18.1 | 95.6 | None |

*The reactant feed rate is in milliters of liquid olefin per hour, whereas the CO is in milliters of gaseous CO per hour. The numbers in ( ) are the weight percent CO based on weight of feed.

This example demonstrates the effectiveness of low levels of CO addition to the reactant feed for elimination of polymer formation during the desired disproportionation reaction.

EXAMPLE III

Freshly distilled 1,5,9-cyclododecatriene was passed through a guard bed containing about 80 g of 13X molecular sieve and 67 g of MgO (equal volumes), then reacted with an excess of ethylene at about 345° C. and 30 WHSV (based on active catalyst) over 1.5 g $WO_3$-$SiO_2$ (Davison SMR-7-2870) admixed with 4.5 g $Al_2O_3$ (Norton SA-5123). Catalyst was pre-treated as described above, heating in air maintained for about 14 hours before CO pre-treatment and cooling to reaction temperature. As indicated in Table III, Run 1, in the absence of CO, inhibitor-free reactant causes reactor

TABLE I

| Run No. | Catalyst | Reactant (mol ratio) | Feed Rate** Olefin, mL/hr | CO, mL/min | | Reaction Conditions Temp., °C. | Press., psig | Time, hr | WHSV | Conversion | Total Selectivity | Polymer |
|---|---|---|---|---|---|---|---|---|---|---|---|---|
| 1 | A' | 1-hexene/1-octene (1:1) | 30 | — | | 130 | 100 | 4 | 1 | 39.9 | 57.4 | Yes |
| 2 | A" | 1-hexene/1-octene (1:1) | 30 | — | | 130 | 100 | 4 | 1 | 59.2 | 37.7 | Yes |
| 3 | A'"* | 1-hexene/1-octene (1:1) | 30 | — | | 130 | 100 | 6 | 1 | 20.8 | 34.6 | Yes |
| 4 | A' | 1-hexene/1-octene (1:1) | 30 | 64 | (23) | 130 | 100 | 6 | 1 | 54.9 | 59.4 | None |
| 5 | A | 1-hexene/1-octene (1:1) | 30 | 64 | (23) | 130 | 100 | 3 | 1 | 55.4 | 79.6 | None |
| 6 | A | 1-hexene/1-octene (1:1) | 145 | 35 | (2.6) | 130 | 75 | 2 | 5 | 55.7 | 76.7 | None |
| 7 | A | 1-hexene/1-octene (1:1) | 30 | 64 | (23) | 130 | 100 | 2 | 1 | 72.3 | 61.7 | None |
| 8 | A" | 1-hexene/1-octene (1:1) | 30 | 50 | (18) | 130 | 85 | 4 | 1 | 63.0 | 50.6 | None |
| 9 | A | 1-hexene/1-octene (1:3) | 150 | 42 | (3.0) | 130 | 80 | 3 | 10 | 26.9 | 84.8 | None |

*Catalyst not CO pretreated.
**The reactant feed rate is in milliters of liquid olefin per hour, whereas the CO is in milliters of gaseous CO per hour. The numbers in ( ) are the weight percent CO based on weight of feed.

These results demonstrate that the presence of CO in the olefin feed introduced to the reactor prevents polymer formation during the disproportionation reaction. Conversions and selectivities are comparable to or better than results obtained in the absence of CO co-feed.

plugging after about 3-4 hours on stream. Other runs in the absence of CO employing variously purified feeds show variable incidence of polymer formation. When reaction is carried out in the presence of CO co-feed, polymer formation is not observed.

TABLE III

| Run No. | CDT, mL/hr | Ethylene, mL/hr | CO, mL/min | | Ethylene/CDT mol ratio | Press., psig | Time, hr | Conversion | Selectivity | Polymer |
|---|---|---|---|---|---|---|---|---|---|---|
| 1 | 55[a,b] | 66 | — | | 10/1 | 50 | 2 | 26.8 | 70.9 | None |
|   |   |   |   |   |   |   | 3 | 25.3 | 31.7 | None |
|   |   |   |   |   |   |   | 3.5 | 25.0 | 17.3 | Yes |
| 2 | 55[c,b] | 66 | — | | 10/1 | 50 | 5 | 91.9 | 64.1 | None |
|   |   |   |   |   |   |   | 12 | 82.5 | 51.3 | None |
| 3 | 55[c] | 66 | — | | 10/1 | 50 | 3 | 89.8 | 61.9 | None |
|   |   |   |   |   |   |   | 5 | 80.7 | 57.9 | Yes |
|   |   |   |   |   |   |   | 7 | 83.4 | 52.5 | None |
| 4 | 55[b] | 66 | — | | 10/1 | 50 | 2 | 73.5 | 32.5 | None |
|   |   |   |   |   |   |   | 3 | 45.5 | 24.9 | Yes |
| 5 | 55[b] | 66 | 50 | (3) | 10/1 | 50 | 4.5 | 67.2 | 43.5 | None |
|   |   |   |   |   |   |   | 9 | 45.5 | 32.9 | None |
|   |   |   |   |   |   |   | 12 | 32.2 | 24.2 | None |
| 6[d] | 45[a] | 55 | 42 | (3) | 10/1 | 50 | 4.5 | 87.6 | 56.7 | None |
|   |   |   |   |   |   |   | 12 | 82.4 | 50.6 | None |
| 7 | 55[b] | 102 | 50 | (2) | 15/1 | 500 | 4 | 74.3 | 36.0 | None |
|   |   |   |   |   |   |   | 11 | 74.1 | 34.8 | None |
| 8[d] | 45[b] | 82.5 | 10 | (0.5) | 15/1 | 500 | 4 | 77.5 | 38.5 | None |
| 9 | 55[c] | 66 | 50 | (3) | 10/1 | 50 | 4.5 | 85.6 | 44.4 | None |
|   |   |   |   |   |   |   | 12 | 76.9 | 36.1 | None |

[a]Distilled
[b]Percolated through guard bed (105 g 13× molecular sieve; 45 g MgO).
[c]Flash distilled.
[d]17% less active catalyst used (1.25 g vs. 1.5 g WO$_3$.SiO$_2$).
[e]The reactant feed rate is in milliliters of liquid olefin per hour, whereas the CO is in milliliters of gaseous CO per minute. The number in ( ) are the weight percent CO based on weight of feed.

This example illustrates the effectiveness of low levels of CO for reduction of polymer formation in the disproportionation of 1,5,9-cyclododecatriene in the presence of ethylene. None of the runs employing CO as co-feed evidenced polymer plugging or precipitation.

While this invention has been described in detail for the purpose of illustration, it is not to be construed as limited thereby but is intended to cover all changes and modifications within the spirit and scope thereof.

We claim:

1. A method of cleaving a cyclic olefin to give a product comprising at least one diolefin comprising: introducing carbon monoxide into a reaction zone along with a feed comprising said cyclic olefin and ethylene unnder disproportionation conditions; and recovering said at least one diolefin product.

2. A method according to claim 1 wherein said carbon monoxide is introduced in an amount within the range of 0.1 to 50 weight percent based on the weight of said feed.

3. A method according to claim 1 wherein said method is carried out utilizing a catalyst consisting essentially of alumina and between 0.1 and 30 weight percent of molybdenum oxide based on the weight of the total catalyst.

4. A method according to claim 1 wherein said method is carried out utilizing a cobalt-molybdenum catalyst on alumina.

5. A method according to claim 1 wherein said method is carried out utilizing a tungsten compound as the catalyst.

6. A method according to claim 5 wherein said catalyst comprises WO$_3$.SiO$_2$.

7. A method according to claim 1 wherein said cyclic olefin is 1,5,9-cyclododecatriene and said product diolefin product comprises 1,5-hexadiene.

8. A method according to claim 1 wherein said method is carried out utilizing a fixed bed reactor and a weight hourly space velocity within the range of 0.5 to 20 parts weight of feed per part by weight of catalyst per hour.

9. A method for synthesizing bis(cycloalkenyl)-substituted olefins which comprises:
passing an alkenyl-substituted cycloalkene having the formula

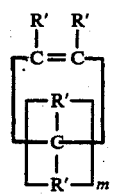

wherein one R' is

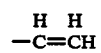

wherein the remaining R's are selected from the group consisting of hydrogen and alkyl radicals containing from 1 to 10 carbon atoms, wherein m is 4, and wherein the total carbon atoms in one of said alkenyl-substituted cycloalkenes does not exceed 20 to a reaction zone along with 0.1 to 50 weight percent CO based on the weight of said alkenyl-substituted cycloalkene;

contacting said alkenyl-substituted cycloalkene with an effective catalytic amount of a catalyst resulting from the admixture of one of molybdenum oxide, cobalt oxide, tungsten oxide, molybdenum hexacarbonyl, tungsten hexacarbonyl, ammonium tungstate, and molybdenum, cobalt and tungsten materials convertible to the oxide on calcination and one of alumina- and silica-containing support under conditions of temperature and pressure sufficient to form bis(cycloalkenyl)-substituted olefins of the formula

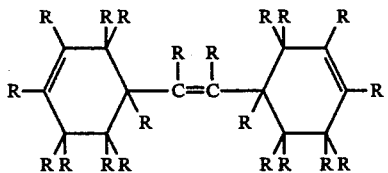

wherein R is at least one member selected from the group consisting of hydrogen and alkyl containing from 1 to 10 carbon atoms; and recovering said bis(cycloalkenyl)-substituted olefin.

10. A method according to claim 9 wherein said catalyst is pretreated with CO prior to contact with said alkenyl-substituted cycloalkene.

11. A method according to claim 9 wherein the said alkenyl-substituted cycloalkene is contacted with said catalyst at a temperature ranging from 25°–300° C. and at pressures ranging from 0–1500 psig.

12. A method according to claim 9 wherein the catalyst consists essentially of alumina and between 0.1 and 30 weight percent of molybdenum oxide.

13. A method according to claim 9 wherein said catalyst comprises a mixture of 3 to 15 weight percent molybdenum oxide, 1 to 5 weight percent cobalt oxide and 96 to 80 weight percent aluminum oxide.

14. A method according to claim 9 wherein the said alkenyl-substituted cycloalkene is contacted with the said catalyst in the presence of a diluent.

15. A method according to claim 9 wherein 1,2-bis(3-cyclohexen-1-yl)ethylene is formed by contacting 4-vinylcyclohexene with a catalyst consisting essentially of from 3 to 15 weight percent molybdenum oxide, 1 to 5 weight percent cobalt oxide and from 96 to 80 weight percent aluminum oxide which aluminum oxide has a surface area ranging from 25–300 square meters per gram at a temperature ranging from 75°–200° C. for a period of time sufficient to obtain a 25 percent conversion and recovering the 1,2-bis(3-cyclohexen-1-yl)-ethylene product.

* * * * *